United States Patent
Zhang

(10) Patent No.: US 8,162,838 B2
(45) Date of Patent: Apr. 24, 2012

(54) DOPPLER SIGNAL SPECTRUM CALCULATING METHOD AND APPARATUS

(75) Inventor: Yu Zhang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 524 days.

(21) Appl. No.: 12/169,512

(22) Filed: Jul. 8, 2008

(65) Prior Publication Data

US 2009/0030319 A1    Jan. 29, 2009

(30) Foreign Application Priority Data

Jul. 11, 2007    (CN) .......................... 2007 1 0137259

(51) Int. Cl.
*A61B 8/00*    (2006.01)
(52) U.S. Cl. ......... 600/454; 600/453; 600/437; 600/407
(58) Field of Classification Search .................. 600/454, 600/455, 457, 468, 465, 479
See application file for complete search history.

(56) References Cited

U.S. PATENT DOCUMENTS

| 4,770,184 | A | * | 9/1988 | Greene et al. ................. 600/454 |
| 5,437,281 | A | * | 8/1995 | Lin et al. ....................... 600/443 |
| 6,306,093 | B1 | * | 10/2001 | Wang ............................. 600/454 |
| 2001/0024311 | A1 | * | 9/2001 | Larkin et al. .................. 359/237 |
| 2003/0100833 | A1 | * | 5/2003 | He et al. ........................ 600/446 |
| 2003/0158484 | A1 | * | 8/2003 | Pan et al. ....................... 600/453 |

* cited by examiner

*Primary Examiner* — Tse Chen
*Assistant Examiner* — Joel F Brutus
(74) *Attorney, Agent, or Firm* — Kory D. Christensen; Stoel Rives LLP

(57) ABSTRACT

A method and apparatus is disclosed for calculating a Doppler signal spectrum. The method includes a step of estimating parameters of a Doppler signal, and a step of resolving a predefined spectrum function using the parameters, the spectrum function being at least a function of the parameters characterizing the strength, frequency center, and frequency deviation of the Doppler signal. The apparatus includes an estimating module, a smoothing module, and a calculating module. According to the Doppler signal spectrum calculating method and apparatus of the present disclosure, the obtained spectrogram has very high time and frequency resolution without requiring any complicated operation. Thus, a higher quality spectrogram can be obtained at a very low cost.

3 Claims, 5 Drawing Sheets

DOPPLER SIGNAL SPECTRUM CALCULATING METHOD AND APPARATUS

CROSS-REFERENCE TO RELATED APPLICATIONS

This application claims priority to Chinese Patent Application No. 200710137259.0, filed Jul. 12, 2007, for "Doppler Signal Spectrum Calculating Method and Apparatus," the disclosure of which is fully incorporated herein by reference.

TECHNICAL FIELD

The present disclosure relates to a Doppler signal spectrum calculating method and apparatus, and more particularly, to a method and apparatus for calculating the signal spectrum of Doppler blood-flow or tissue in an ultrasound diagnostic system.

SUMMARY

A Doppler signal spectrum calculating method and apparatus, which estimates the power spectrum of a Doppler signal based directly on the estimated mean frequency, power, and bandwidth of the Doppler signal by using an analysis function model, is disclosed.

DETAILED DESCRIPTION

Figure 1:
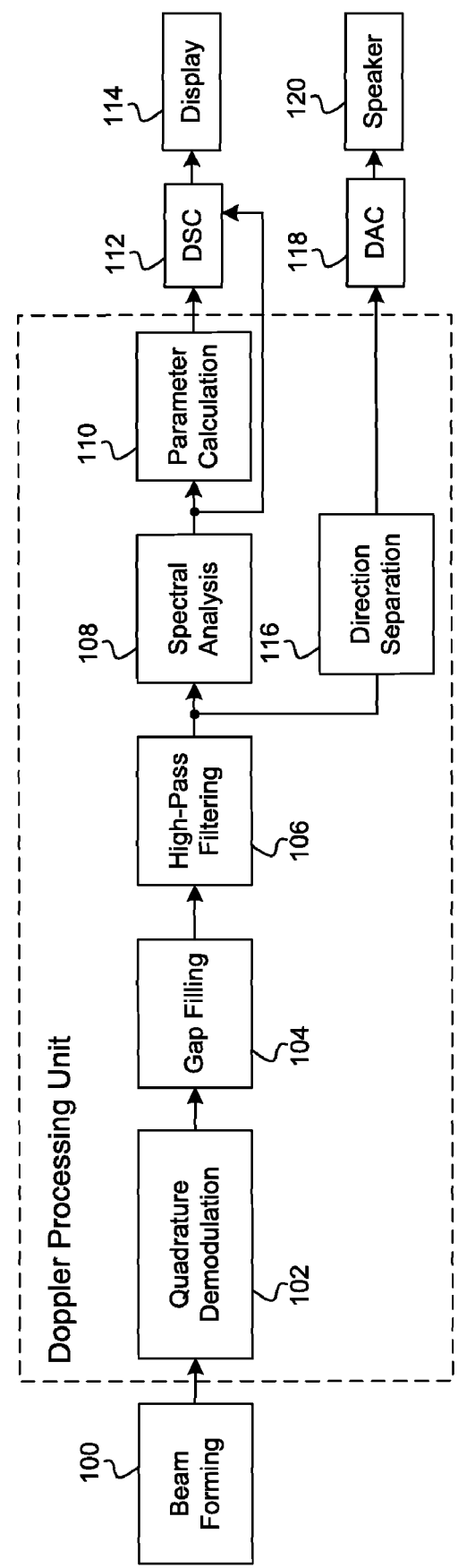
FIG. 1 is a block diagram of Doppler processing units in a typical ultrasound diagnostic imaging system.

The spectral Doppler technique is widely used for non-invasive detection and measurement of blood-flow (or tissue movement) velocity in a human body. In detecting an ultrasound Doppler blood-flow signal, an electrical signal is converted into an ultrasound signal by using a transmitting transducer. Scattering will occur when ultrasound signals meet body cells (e.g., tissue cells or blood cells). Some of the scattered signals will reach a receiving transducer, which will convert the scattered sound signals back into electrical signals. The received weak electrical signals will be subjected to low-noise amplification, quadrature demodulation, and low-pass filtering, in order to obtain two channels of audio quadrature Doppler signals.

Since the echo of a tissue or blood vessel wall has a scattering amplitude much larger than that of a blood cell, the obtained quadrature Doppler signal will be often exposed first to a high-pass filter (which is also referred to as a wall filter) to filter out the tissue and vessel wall echo signals having very low frequencies. The spectral analysis of the obtained Doppler signal will lead to a power spectrum of this signal. The evaluation of power spectra of Doppler signals at various times will result in a spectrogram of the Doppler signals, which can then be sent to a display device. Meanwhile, the quadrature Doppler signals are subjected to direction separation in order to obtain audio Doppler signals that correspond to the forward blood-flow and the reverse blood-flow, respectively. The audio Doppler signals are respectively sent to the left and right channels of stereo loudspeakers for outputting. Furthermore, a mean frequency curve and a maximum frequency curve can be extracted from the spectrogram, from which some important clinical diagnostic parameters will also be calculated.

Existing diagnostic ultrasound systems usually calculate the power spectrum of a Doppler signal by performing the Fourier transformation of the Doppler signal. Prior to the calculation of the spectrum, a segment of the quadrature Doppler signal is first weighted by means of a window function. The windowed signal is calculated by means of FFT with a fixed length (e.g., 256 points), and the calculated coefficient is then amplitude squared. When the length of the signal is less than the number of points calculated by means of FFT, the windowed signal is padded with zeros, such that the length of the padded signal is the exact number of points (e.g., 256 points) as is required for the FFT calculation. The time and frequency resolution of the spectrogram obtained by the above calculation completely depends on the kind and length of the window function. Since the kind of a window function is usually fixed, the length of a window function will determine the resolution of the spectrogram.

To guarantee a better time resolution of the displayed spectrogram, the length of a window function will be often related to the sampling rate of the Doppler signal (i.e., pulse repetition frequency of the pulse Doppler signal or the sampling rate of the continuous wave Doppler signal) and the time interval of adjacent spectral line updates. For example, as the signal sampling rate increases, the length of a window function increases; as the time interval of adjacent spectral line updates increases, the length of a window function increases.

However, when the movement velocity of a target to be detected is relatively low (e.g., the signal sampling rate falls below 1 kHz), and the spectral line update time required is relatively short (e.g., the spectral line update interval is 4 ms), in order to realize a better time resolution, the window function required by the above-mentioned traditional method is very short, which significantly reduces the frequency resolution of the spectrum, and results in a large velocity estimation error.

Alternatively, an autoregressive model (i.e., an AR model) may also be used to model an ultrasound Doppler signal, and the spectrum of the signal will also be obtained by Z transforming the parameters of the AR model (or using the FFT to implement a fast Z transformation). Since an AR model is a pure pole model and a very large spectrum peak will be produced at the frequency corresponding to a pole, the power spectrum calculated by directly using the parameters of an AR model will have a very wide dynamical range, and the power spectrum curve that changes with the signal bandwidth will change greatly. Therefore, the spectrogram will appear unnatural.

U.S. Pat. Nos. 6,030,345 and 6,306,093 propose, by combining the two above-mentioned approaches, a method of using an AR model to model the obtained Doppler signal, and then using the AR model to predict and estimate the signal outside the segment (i.e., implementing an extrapolation), and performing windowing and FFT calculation after concatenating the obtained signal with the extrapolated signal.

This method solves the problem with the time and frequency resolution to a certain extent, and the display modality of the spectrogram will also be the same as that obtained via a traditional FFT based approach. However, the AR model parameter estimation and the signal prediction will greatly increase the implementation cost, and the estimated deviation of the AR model parameter may cause the extrapolated signal and the concatenated signal to have different frequency information and may finally introduce some noise on the spectrogram display.

With respect to these disadvantages with existing technologies, the present disclosure provides a Doppler signal spectrum calculating method and apparatus, which estimates the power spectrum of a Doppler signal based directly on the estimated average frequency, power and bandwidth of the Doppler signal by using an analysis function model.

According to a first aspect of the present disclosure, there is provided a method for calculating the Doppler signal spectrum. The method may include estimating parameters of a Doppler signal, the parameters being used to characterize the strength, frequency center, and frequency deviation of the Doppler signal. The method may further include resolving a predefined spectrum function using the parameters, the spectrum function being at least a function of the parameters characterizing the strength, frequency center, and frequency deviation of the Doppler signal.

Optionally, the method may further include a step of smoothing the estimated parameters. In one embodiment, the smoothing processing involves linear or nonlinear filtering. The parameters may include the power, mean frequency, and bandwidth of the Doppler signal. One or more of the estimated power, mean frequency, and bandwidth is smoothed.

In one configuration, autocorrelation is used to perform the parameter estimation. Alternatively, a first order AR model is used to perform the parameter estimation.

The predefined spectrum function may be a continuous function of frequency. The continuous function of the frequency may be a Gaussian function, wherein the amplitude of the Gaussian function depends on the parameter that characterizes the strength of the Doppler signal, the center of the Gaussian function depends on the parameter that characterizes the frequency center of the Doppler signal, and the width of the Gaussian function depends on the parameter that characterizes the frequency deviation of the Doppler signal.

According to another aspect of the present disclosure, there is provided an apparatus for calculating a Doppler signal spectrum. The apparatus may include an estimating module for performing parameter estimation of a Doppler signal, the parameters being used to characterize the strength, frequency center, and frequency deviation of the Doppler signal. The apparatus may further include a calculating module for resolving a predefined spectrum function using the parameters, the spectrum function being at least a function of the parameters characterizing the strength, frequency center, and frequency deviation of the Doppler signal.

Optionally, the apparatus may further include a smoothing module for smoothing the estimated parameters. In one embodiment, the smoothing module is a linear or nonlinear filter. The parameters may include the power, mean frequency, and bandwidth of the Doppler signal. The smoothing module smoothes one or more of the estimated power, mean frequency, and bandwidth.

In one embodiment, the estimating module uses autocorrelation to perform the parameter estimation, or uses a first order AR model to perform the parameter estimation.

According to the Doppler signal spectrum calculating method and apparatus of the present disclosure, the obtained spectrogram has very high time and frequency resolution without requiring any complicated operation, such as parameter estimation by using a higher order AR model parameter estimation or 256-point FFT calculation, etc. Thus, a higher quality spectrogram may be obtained at very low cost.

1. Method of Calculating Doppler Signal Spectrum

A typical arrangement of Doppler processing units in an ultrasound diagnostic imaging system is shown in FIG. 1. Radio frequency ultrasound echo signals are subjected to beam forming 100, and are then subjected to quadrature demodulation 102 to obtain I (in-phase) and Q (quadrature) Doppler signals. When the system operates in dual imaging mode (two-dimension imaging mode and spectral Doppler mode at the same time), Doppler signal gaps may exist in the 2D imaging interval, and gap filling 104 should be implemented to obtain continuous spectrum display and sound output. The Doppler signals, after being gap-filled, will be subjected to the high pass filter 106 to remove a number of tissue and vessel wall low frequency clutter signals having large amplitudes. The signals, after being high pass filtered, will be subjected to the spectral analysis 108 to obtain the spectrogram of the Doppler signal.

A maximum frequency curve and mean frequency curve, etc. will be extracted by using the spectrogram, from which some important clinical diagnostic parameters will be calculated 110. These parameters will be subjected to the digital scan convertor 112, after which the spectrogram and the maximum frequency curves will be displayed on the display 114 in real time. The signals, after being high pass filtered, will be subjected to blood-flow direction separation 116 to obtain the Doppler signals of the forward and reverse blood-flow, after which the signals will be subjected to digital-analog convertion 118 and then respectively sent to the left and right channels of the stereo loudspeaker 120 for outputting.

Figure 2:
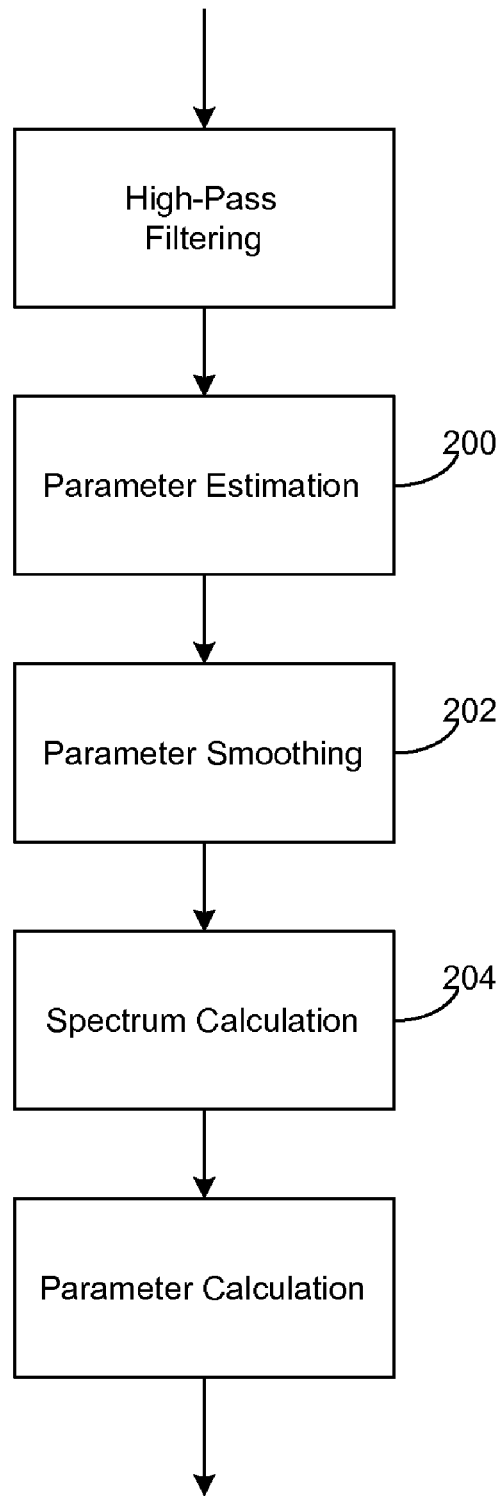
FIG. 2 is a flow diagram of a Doppler signal spectrum calculating method.

A flow diagram of a Doppler signal spectrum calculating method proposed according to embodiments of the present disclosure is shown in FIG. 2. Initially, a segment of signal is selected from the obtained Doppler signal for the parameter estimation (Step 200). The estimated parameters will be used to characterize the strength, frequency center, and frequency deviation of this section of the Doppler signal. The length of the selected signal may be a function of the Doppler signal sampling rate and spectral line update time interval, i.e., the length of the selected signal becomes shorter as the Doppler signal sampling rate decreases, and the length of the selected signal also becomes shorter as the spectral line update time interval becomes shorter. In view of the accuracy of the parameter estimation, the length of the selected signal should not be less than a certain predefined length. In addition, in view of the processing complexity, the length of the selected signal may also be limited to a length less than or equal to a certain predefined length. The estimated parameters may be the power, mean frequency, and bandwidth of the signal. Autocorrelation may be used for parameter estimation as follows:

$$N = \sum_{i=1}^{M-1} (I_i Q_{i+1} - I_{i+1} Q_i), \qquad \text{Eq. 1}$$

$$D = \sum_{i=1}^{M-1} (I_i I_{i+1} + Q_i Q_{i+1}), \qquad \text{Eq. 2}$$

$$R(0) = \sum_{i=1}^{M-1} \frac{I_i^2 + I_{i+1}^2 + Q_i^2 + Q_{i+1}^2}{2}; \qquad \text{Eq. 3}$$

wherein R(O) represents the power of the signal, and M is the length of the selected signal.

Based on parameters N and D, Phase and Magn are computed as follows:

$$\text{Phase} = \tan^{-1}\left(\frac{N}{D}\right), \qquad \text{Eq. 4}$$

$$\text{Magn} = \sqrt{N^2 + D^2}; \qquad \text{Eq. 5}$$

wherein Phase is the mean angular frequency, which is divided by $2\pi$ to obtain normalized digital frequency. Based on Magn and $R(0)$, the variance of the signal may be estimated:

$$\text{var} = 2\left(1 - \frac{\text{Magn}}{R(0)}\right). \qquad \text{Eq. 6}$$

The bandwidth of the signal may be represented as the square root of the above variance:

$$BW = \sqrt{\text{var}}. \qquad \text{Eq. 7}$$

Furthermore, it can be seen from the signal processing analysis that the above parameters obtained by autocorrelation calculation will be exactly equivalent to the parameters obtained by a first order AR model approach, i.e., the phase of the pole of the first order AR model corresponds to Phase, the amplitude of the pole corresponds to the above Magn/$R(0)$, and the calculating approach of the power is also similar. Therefore, both of them can be interchangeably used to calculate the power, mean frequency, and bandwidth of the Doppler signal.

Since there may be errors in the estimated mean frequency, bandwidth, and power due to the influence of the noise and the length of the selected signal, errors can be reduced by smoothing processing (Step 202). Additionally, different smoothing processing may be performed on three parameters. For example, only the bandwidth may be smoothed, without smoothing the mean frequency and power. A linear or nonlinear filtering may be selected for smoothing. For example, a linear digital low pass filter or median filter may be selected to be used for smoothing. The mean frequency, bandwidth, and power being smoothed are applied to a pre-selected power spectrum function for calculation of the power spectrum (Step 204).

In one embodiment, this power spectrum function is a function of the above three parameters and frequency. For better display of the spectrum modality, this function may be required to be a continuous function, that is, the value of this spectrum function continuously varies with the frequency. In this embodiment, a Gaussian function is selected as the power spectrum function:

$$P(f) = \frac{P_0}{BW\sqrt{2\pi}} \exp\left\{-\frac{1}{2}\left(\frac{f - f_0}{BW}\right)^2\right\}; \qquad \text{Eq. 8}$$

wherein $P_0$ refers to the power, BW refers to the bandwidth, and $f_0$ refers to the mean frequency. The spectrogram is usually to display the logarithmically compressed power spectrum:

$$lg(P(f)) = lg\left(\frac{P_0}{BW\sqrt{2\pi}}\right) - \frac{1}{2}\left(\frac{f - f_0}{BW}\right)^2 lg(e). \qquad \text{Eq. 9}$$

Since digital signals are periodical in a frequency domain, the above power spectrum function may further be expressed as:

$$P'(f) = \begin{cases} P(f - f_s), & (f - f_0) > \frac{f_s}{2} \\ P(f + f_s), & (f - f_0) < -\frac{f_s}{2} \\ P(f), & \text{other} \end{cases} \qquad \text{Eq. 10}$$

Once being processed as described above, the signal with possible spectrum aliasing can also be well represented.

2. Apparatus for Calculating Doppler Signal Spectrum

Figure 3:
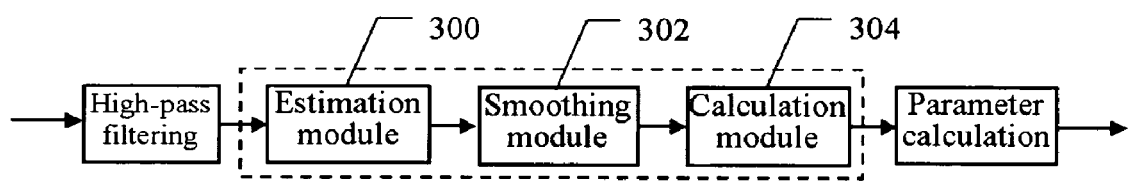
FIG. 3 is a structural schematic diagram of an apparatus for calculating a Doppler signal spectrum.

An apparatus according to embodiments of the present disclosure for calculating the Doppler signal spectrum is shown in FIG. 3, including an estimating module 300, an optional smoothing module 302, and a calculating module 304. The estimating module 300 may be used to perform the parameter estimation of a Doppler signal, the parameters being used to characterize the strength, frequency center and frequency deviation of the Doppler signal. In this embodiment, the estimating module 300 may use autocorrelation to perform the parameter estimation, or use a first order AR model to perform the parameter estimation. The smoothing module 302 may be used to smooth the estimated parameters. In this embodiment, the smoothing module 302 may be a linear filter or nonlinear filter. In addition, the smoothing module 302 can smooth one or more among the estimated power, mean frequency, and bandwidth. The calculating module 304 may use the estimated parameters to resolve the predefined spectrum function, the spectrum function being at least a function of the parameters that characterize the strength, frequency center, and frequency deviation of the Doppler signal. In this embodiment, a Gaussian function is selected as the predefined spectrum function.

Figure 4:
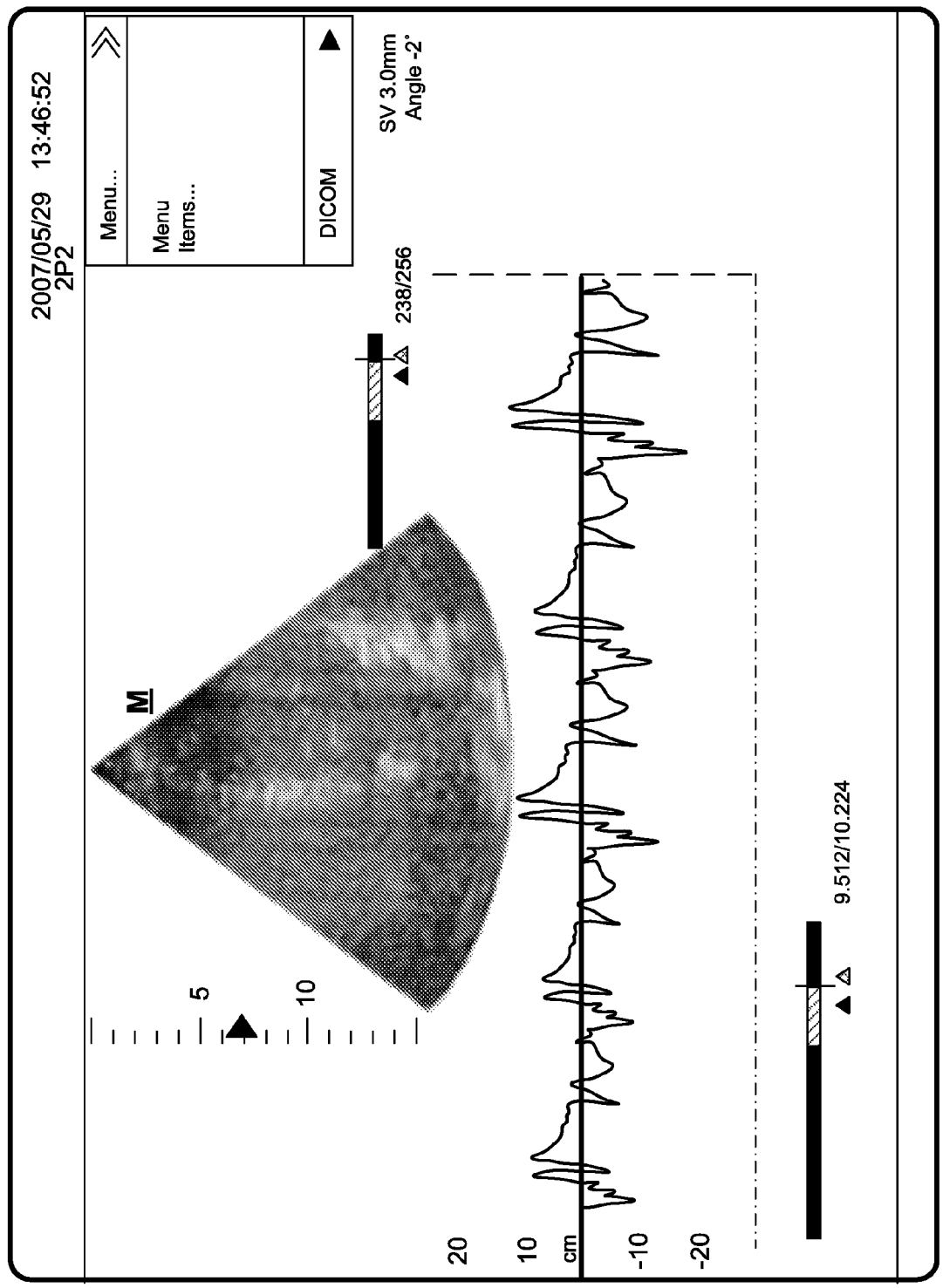
FIG. 4 is a spectrogram obtained by using existing technologies.
Figure 5:
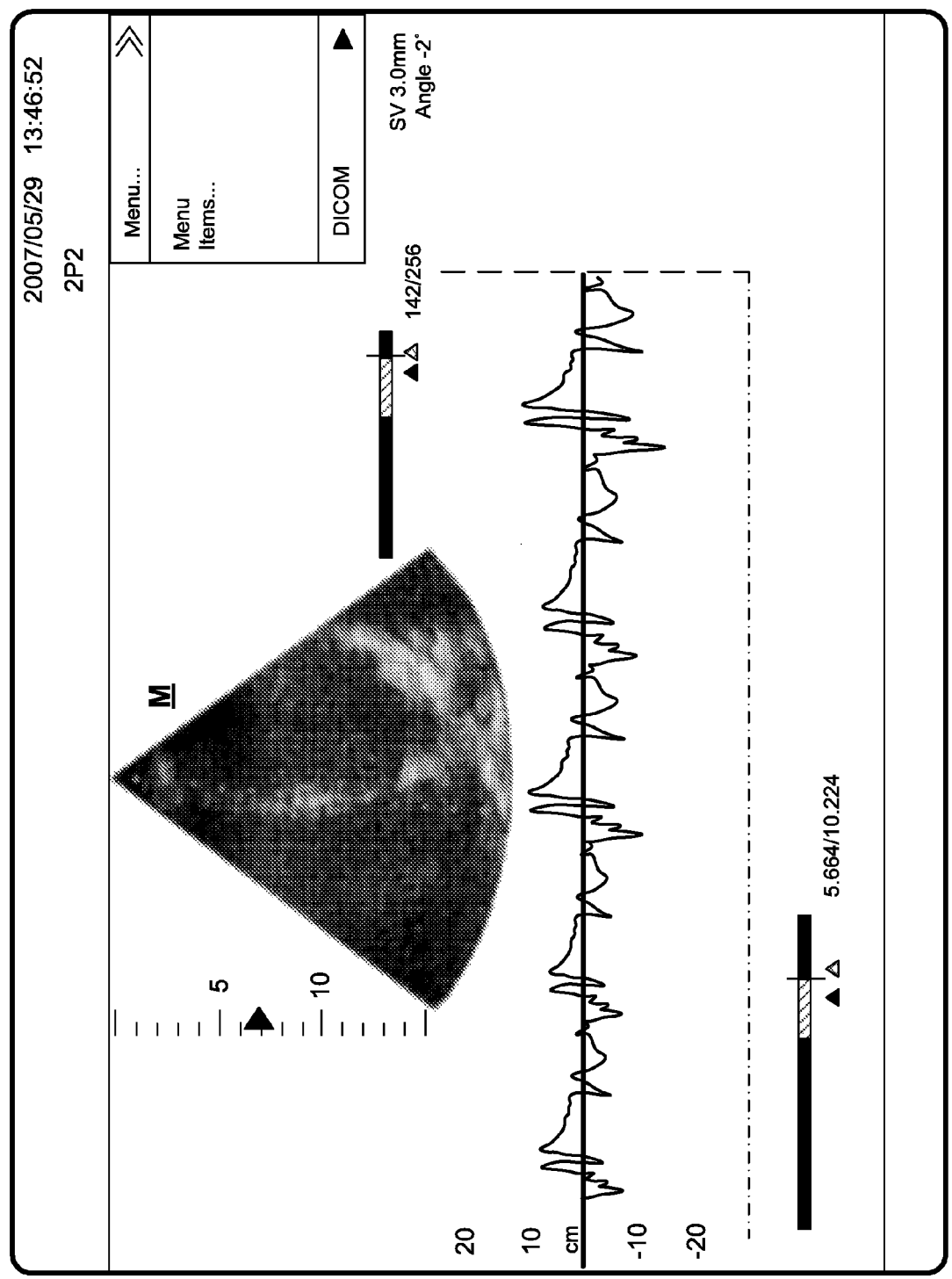
FIG. 5 is a spectrogram obtained by using the disclosed method and apparatus.

FIG. 4 illustrates a Doppler spectrogram of cardiac muscle tissue movement that is obtained by applying an existing FFT based approach. Because the very low velocity of the cardiac muscle tissue movement and the very low sampling rate of the Doppler signal will result in bad time and frequency resolution of the spectrogram obtained, it is impossible to obtain a clear status of the cardiac muscle movement at different times in each cardiac cycle. By contrast, FIG. 5 shows a Doppler spectrogram obtained by the method and apparatus according to the embodiments of the present disclosure, which clearly displays the cardiac muscle movement velocity at various moments in each cardiac cycle, greatly facilitating the clinical diagnosis.

Although the forgoing description includes specific embodiments, the present disclosure will not be limited to the above embodiments. Those skilled in the art of Doppler signal processing may make appropriate additions, reductions, or substitutions to aspects of the processing stages as described in these embodiments in order to achieve a similar effect. For example, a method other than autocorrelation and a first order AR model may be used to estimate and obtain the parameters, such as the mean frequency, etc., of a Doppler signal, or the mean frequency may be replaced by the root mean square frequency, or the Gaussian power spectrum function may be replaced by other continuous functions, and so on. Any modification, addition, reduction, or substitution made on the embodiments without departing from the spirit of the present disclosure, should be regarded as within the scope of the present disclosure.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

As used herein, a software module or component may include any type of computer instruction or computer executable code located within a memory device and/or transmitted as electronic signals over a system bus or wired or wireless network. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

What is claimed is:

1. A non-transitory computer-readable medium comprising program code for causing a computer to perform a method of calculating a Doppler signal spectrum, the method comprising:
    receiving ultrasound echo signals;
    demodulating the ultrasound echo signals to obtain a Doppler signal;
    estimating parameters of the Doppler signal, the parameters comprising the strength, frequency center and frequency deviation of the Doppler signal; and
    resolving a predefined spectrum function of the Doppler signal based directly on the parameters,
    the spectrum function being at least a function of the parameters that characterize the power, mean angular frequency, and frequency deviation of the Doppler signal, where M is the length of the Doppler signal, R(0) represents the power of the signal, and R(0) is calculated as:

$$R(0) = \sum_{i=1}^{M-1} \frac{I_i^2 + I_{i+1}^2 + Q_i^2 + Q_{i+1}^2}{2}.$$

2. The non-transitory computer-readable medium of claim 1, where the mean angular frequency, P, is calculated as:

$$N = \sum_{i=1}^{M-1} (I_i Q_{i+1} - I_{i+1} Q_i), \quad D = \sum_{i=1}^{M-1} (I_i I_{i+1} - Q_i Q_{i+1}), \text{ and}$$

$$P = \tan^{-1}\left(\frac{N}{D}\right).$$

3. The non-transitory computer-readable medium of claim 1, where the frequency deviation, var, is calculated as:

$$Magn = \sqrt{N^2 + D^2}, \text{ and } \text{var} = 2\left(1 - \frac{Magn}{R(0)}\right).$$

* * * * *